(12) United States Patent
Geneste et al.

(10) Patent No.: US 7,927,813 B2
(45) Date of Patent: Apr. 19, 2011

(54) PEPTIDES WHICH INTERACT WITH ANTI-APOPTOTIC MEMBERS OF THE BCL-2 PROTEIN FAMILY, AND USES

(75) Inventors: Olivier Geneste, Rueil-Malmaison (FR); John Hickman, Paris (FR); Jean-Christophe Rain, Ermont (FR)

(73) Assignees: Les Laboratories Servier, Suresnes Cedex (FR); Hybrigenics, Paris (FR)

( * ) Notice: Subject to any disclaimer, the term of this patent is extended or adjusted under 35 U.S.C. 154(b) by 669 days.

(21) Appl. No.: 11/883,400

(22) PCT Filed: Jan. 31, 2006

(86) PCT No.: PCT/FR2006/000206
§ 371 (c)(1),
(2), (4) Date: Jul. 30, 2007

(87) PCT Pub. No.: WO2006/082304
PCT Pub. Date: Aug. 10, 2006

(65) Prior Publication Data
US 2009/0325883 A1 Dec. 31, 2009

(30) Foreign Application Priority Data
Feb. 1, 2005 (FR) ..................................... 05 00978

(51) Int. Cl.
*C07K 14/00* (2006.01)
*G01N 33/53* (2006.01)
*G01N 33/52* (2006.01)
(52) U.S. Cl. ............ 435/7.1; 530/300; 435/7.2; 435/7.8
(58) Field of Classification Search ........................ None
See application file for complete search history.

(56) References Cited

U.S. PATENT DOCUMENTS 7,459,434 B2 * 12/2008 Geneste et al.
7,582,439 B2 * 9/2009 Cory et al.
7,588,914 B2 * 9/2009 Godzik et al.
7,723,469 B2 * 5/2010 Walensky et al.

OTHER PUBLICATIONS

Ninkina et al., Cerd4, third member of the d4 gene family: expression and organization of genomic locus, Mamm. Genome, 12(11):862-866, 2001.*
Oltersdorf et al., An inhibitor of Bcl-2 family proteins induces regression of solid tumours, Nature, 435:667-681, Jun. 2, 2005.*
Delft et al., The BH3 mimetic ABT-737 targest selective Bcl-2 proteins and efficiently induced apoptosis via Bak/Bax if Mcl-1 is neutralized, Cancer Cell, 10:389-399, Nov. 2006.*
J.A. Parsons, Peptide Hormones (University Park Press: Baltimore), pp. 1-7, 1976.*
T.E. Creighton, PROTEINS: Structure and molecular principles (W.H. Reeman & Co.: New York), pp. 223-227, 1984.*
Walensky et al., Activation of Apoptosis in vivo by a hydrocarbon-stapled BH3 helix, Science 305:1466-1470, 2004.*
Viera et al., Pro-apoptotic BH3 peptides, Oncogene 21:1963-1977, 2002.*
Database EMBL, Jun. 18, 1998, "Rattus norvegicus BcI-2 related orvarian death gene product BOD mNRA, Complete CDS." XP002355353, Accession No. EM_PRO:AF065431.
Database UniProt, Nov. 1, 1997, "Zinc-finger protein DPF2 (cer-d4)" XP002355352, Accession No. Q92784.
Database UnitProt, Oct. 25, 2004, "HECT, UBA and WWE domain containing protein 1(E3 ubiquitin protein ligase URE-B1) (Mcl-1 ubiquitin ligase E3) (Mule) (ARF-binding protein 1) (ARF-BP1)" XP002355987, Accession No. Q7Z6Z7.
Database UniProt, Mar. 29, 2004, "DNA replication complex GINS protein PSF2" XP002355988, Accession No. Q9Y248.
Database UniProt, Jul. 5, 2004, "Mineral dust induced gene protein 2" XP002355989, Accession No. Q6SKSO.
Ottilie S. et al., "Dimerization properties of human BAD. Identification of a BH-3 domain and analysis of its binding to mutant BCL-2 and BCL-XL proteins", Journal of Biological Chemistry, vol. 272, No. 49, p. 30866-30872, Dec. 5, 1997.
Inohara N., et al., "Harakiri, a novel regulator of cell death, encodes a protein that activates apoptosis and interacts selectively with survival-promoting proteins Bcl-2 and Bcl-X1" EMBO Journal, vol. 16, No. 7, p. 1686-1694, Apr. 1997.
Wang K. et al., "BID: A novel BH3 domain-only death agonist" Genes and Development, vol. 10, No. 22, p. 2859-2869, Nov. 15, 1996.
Boyd J.M., et al., "BIK, A novel death inducing protein shares a distinct sequence motif with bel-2 family proteins and interacts with viral and cellular survival-promoting proteins", Oncogene, Basingstoke, Hants, vol. 11, No. 9, p. 1921-1928, Nov. 2, 1995.
Cory Suzanne, et al., "The Bcl2 family: regulators of the cellular life-or-death switch" Nature Reviews Cancer, vol. 2, No. 9, p. 647-656, Sep. 2002.
Owicki J.C., "Fluorescence polarization and anisotropy in high throughput screening: Perspectives and primer" Journal of Biomolecular Screening, vol. 5, No. 5, p. 297-306, Oct. 2000.
French Preliminary Search Report for FR0500978 of Nov. 25, 2005.
International Search Report for PCT/FR2006/000206 of Sep. 18, 2006.

* cited by examiner

*Primary Examiner* — Lorraine Spector
*Assistant Examiner* — Claire Kaufman
(74) *Attorney, Agent, or Firm* — Hueschen and Sage

(57) ABSTRACT

The invention relates to a method of screening and identifying modulators of the protein interaction between new peptides and anti-apoptotic members of the Bcl-2 protein family. The modulators identified on the basis of this method are administered to patients with cancer in order to bring about apoptotic-type and/or autophagic-type programmed cell death in those patients.

5 Claims, 5 Drawing Sheets

Figure 1: amino acid sequence SEQ ID NO.1 of the Cerd4 peptide which interacts with anti-apoptotic members of the Bcl-2 protein family.

Met Ala Thr Val Ile His Asn Pro Leu Lys Ala Leu Gly Asp Gln Phe Tyr
M   A   T   V   I   H   N   P   L   K   A   L   G   D   Q   F   Y

Lys Glu Ala Ile Glu His Cys
K   E   A   I   E   H   C

Figure 2: amino acid sequence SEQ ID NO.2 of the Kiaa 1578 peptide which interacts with anti-apoptotic members of the Bcl-2 protein family Val Met Thr Gln Glu Val Gly Gln Leu Leu Gln Asp Met Gly Asp Asp Val
V   M   T   Q   E   V   G   Q   L   L   Q   D   M   G   D   D   V Tyr Gln Gln Tyr Arg Ser Leu
Y   Q   Q   Y   R   S   L

Figure 3: amino acid sequence SEQ ID NO.3 of the Genematch peptide which interacts with anti-apoptotic members of the Bcl-2 protein family Arg Leu Lys His Ser Cys Leu Leu Ala Leu Lys Arg Ala Ala Asp Leu Leu
R   L   K   H   S   C   L   L   A   L   K   R   A   A   D   L   L Gly Gln Arg Ser Ser Ser Thr
G   Q   R   S   S   S   T

Figure 4: amino acid sequence SEQ ID NO.4 of the LOC51659 peptide which interacts with anti-apoptotic members of the Bcl-2 protein family Asp Met Trp Asp Thr Arg Ile Ala Lys Leu Arg Val Ser Ala Asp Ser Phe
 D   M   W   D   T   R   I   A   K   L   R   V   S   A   D   S   F Val Arg Gln Gln Glu Ala
 V   R   Q   Q   E   A

Figure 5: amino acid sequence SEQ ID NO.5 of the Mina53 peptide which interacts with anti-apoptotic members of the Bcl-2 protein family Val Ala Thr Arg Arg Leu Ser Gly Phe Leu Arg Thr Leu Ala Asp Arg Leu
 V   A   T   R   R   L   S   G   F   L   R   T   L   A   D   R   L Glu Arg Thr Lys Glu Leu Leu
 E   G   T   K   E   L   L

Figure 6: Consensus motif of the peptide sequences SEQ ID NO.1 to SEQ ID NO.5 according to the invention.

```
XXXXXXXXLXXXXDXXXXXXXXXX
XMATVIHNPLKALGDQFYKEAIEHC
VMTQEVGQLLQDMGDDVYQQYRSLX
RLKHSCLLALKRAADLLGQRSSSTX
DMWDTRIAKLRVSADSFVRQQEAXX
VATRRLSGFLRTLADRLEGTKELLX
```

Figure 7 : determination of Ki, using fluorescence polarisation, of the competitor peptides having amino acid sequences SEQ ID NO.1 (Cerd4), SEQ ID NO. 2 (Kiaa 1578), SEQ ID NO.3 (Genematch), SEQ ID NO.4 (Loc 51659) and SEQ ID NO.5 (Mina 53) according to the invention with respect to the interaction between the pro-apoptotic Bak peptide and anti-apoptotic members such as Bcl-$X_L$.
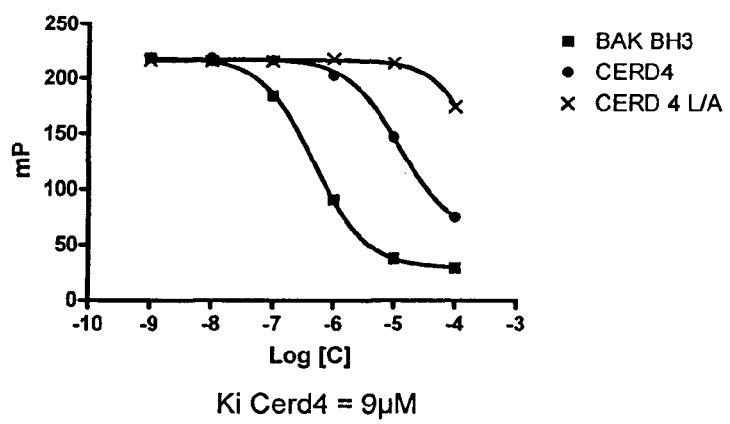
Ki Cerd4 = 9µM
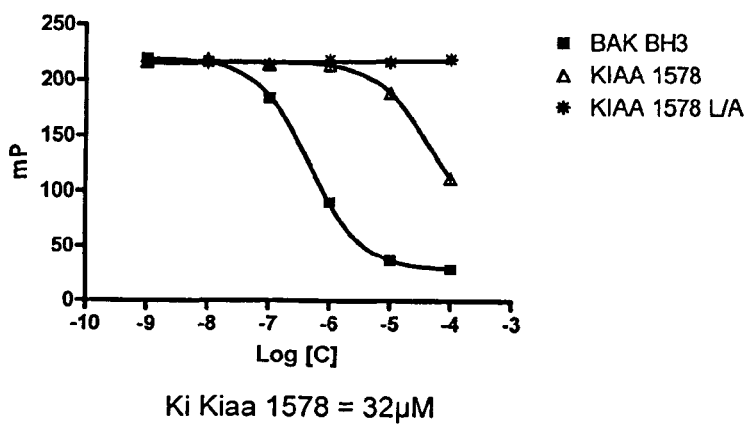
Ki Kiaa 1578 = 32µM

Figure 7 Continued
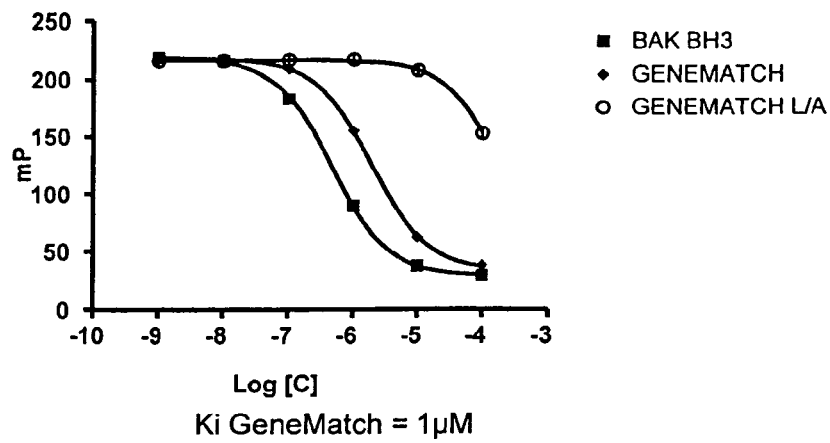
Ki GeneMatch = 1μM
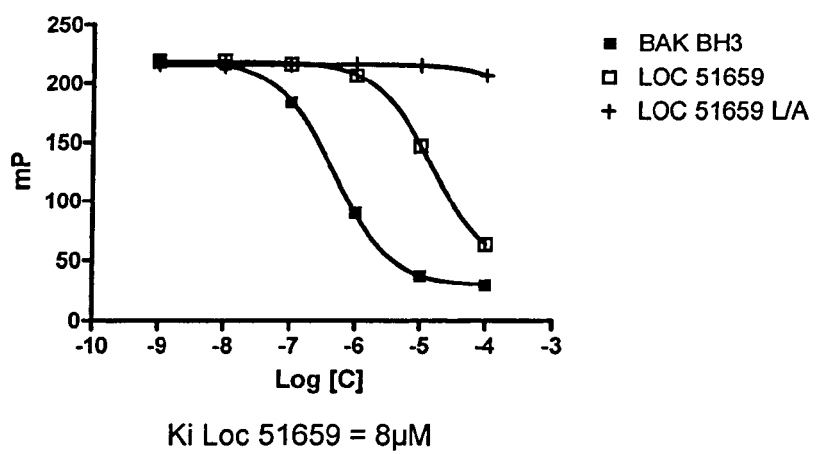
Ki Loc 51659 = 8μM
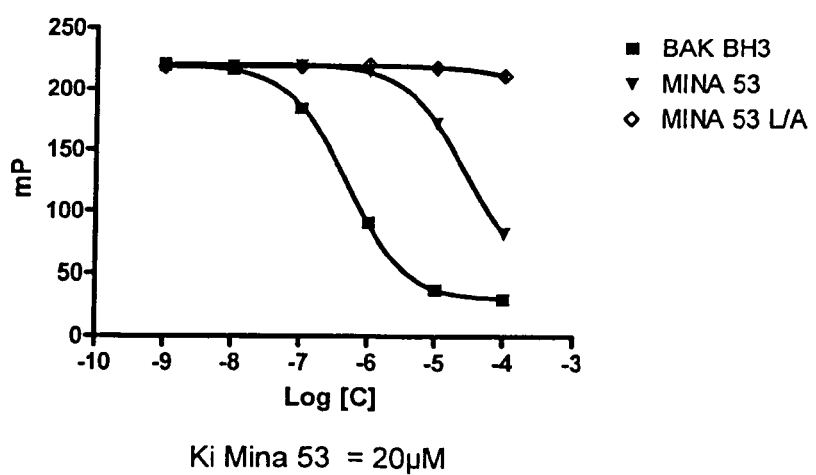
Ki Mina 53 = 20μM

| Peptides | SEQ ID NO | Amino acid sequence | SEQ ID NO | Nucleic acid sequence |
|---|---|---|---|---|
| Cerd4 | SEQ ID NO.1 | MATVIHNPLKALGDQFYKEAIEHC | SEQ ID NO.7 | atggcgactgtcattcacaacccctgaaagcgctcggggaccagttcacaaggaa gccattgagcactgc |
| Kiaa 1578 | SEQ ID NO.2 | VMTQEVGQLLQDMGDDVYQQYRSLX | SEQ ID NO.8 | gttatgacccaagaggttggccagctcctgcaagacatgggtgatgatgtataccagcag taccggtcactt |
| Genematch | SEQ ID NO.3 | RLKHSCLLALKRAADLLGQRSSSTX | SEQ ID NO.9 | agacttaaacattcctgctctgctctgaagagagcagcggatcctctaggacagcgc tcaagctctact |
| Loc51569 | SEQ ID NO.4 | DMWDTRIAKLRVSADSFVRQQEA | SEQ ID NO.10 | gatatgtgggacactcgtatagccaaactccgagtgtctgctgacagctttgtgagacag caggaggca |
| Mina 53 | SEQ ID NO.5 | VATRRLSGFLRTLADRLEGTKELLX | SEQ ID NO.11 | gttgctacaagacgattaagtggcttcctgagacacttgcagaccggctgagggcacc aaagaactgctt |

Figure 8: Recapitulatory table of the amino acid sequences SEQ ID NO.1 to SEQ ID NO.5 and their respective nucleic acid sequences SEQ ID NO.7 to SEQ ID NO.11.

PEPTIDES WHICH INTERACT WITH ANTI-APOPTOTIC MEMBERS OF THE BCL-2 PROTEIN FAMILY, AND USES

The present invention lies within the field of seeking out and identifying new peptides which interact with anti-apoptotic members of the Bcl-2 protein family.

The invention relates to a method of screening and identifying modulators of the protein interaction between those new peptides and anti-apoptotic members of the Bcl-2 protein family. The modulators isolated by this method of screening are useful in regulating apoptotic-type and/or autophagic-type programmed cell death. These modulators are administered to patients in the course of treating cancers.

The invention relates to five peptide motifs each capable of interacting with an anti-apoptotic member of the Bcl-2 protein family and to their uses in bringing about programmed cell death in patients with cancers.

Programmed cell death is composed of, on the one hand, apoptosis and, on the other hand, autophagic death. Apoptosis is the better known phenomenon. This type of cell death involves morphological changes, such as nuclear condensation and DNA fragmentation, and also biochemical phenomena, such as activation of caspases which then degrade key structural components of the cell so as to bring about its disassembly and death. Regulation of the process of apoptosis is complex and involves the activation or repression of several intracellular signalling pathways. Autophagic death is a second, less well-known mechanism of programmed cell death. On the cellular level, autophagy, can be summarised by three stages: formation of an initial autophagic vacuole (the autophagosome) and maturation of the autophagosome into a degradative vacuole and then the fusion thereof with the lysosome. Autophagic death accordingly involves lysosomal degradation processes which are characterised by the accumulation of autophagic vacuoles and which are independent of a caspase-type regulation pathway.

Keeping a cell alive or programming its death necessitates regulation of a major signalling pathway involving, in particular, proteins of the Bcl-2 family.

Proteins of the Bcl-2 family are divided into three main classes. The anti-apoptotic proteins, such as Bcl-2, Bcl-$X_L$ and Bcl-W, have a high degree of homology in their four BH domains. The pro-apoptotic proteins are divided into two categories: on the one hand, the multi-domain proteins such as BAX and BAK and, on the other hand, pro-apoptotic proteins such as BID, NOXA, PUMA, BIK, BIM and BAD which are characterised by the presence of a single homologous domain, the BH3 motif (Cory and Adams, *The Bcl-2 family: regulators of the cellular life-or-death switch* Nature reviews vol. 2 September 2002).

The BH3 motif is an amphiphilic α-helical region whose identity of sequences in the Bcl-2 protein family is relatively low. Furthermore, the presence of the BH3 motif is required in a protein in order to allow interaction with anti-apoptotic members of the Bcl-2 protein family. In fact, the activity of an anti-apoptotic member of the Bcl-2 protein family is regulated by the product of pro-apoptotic genes of said family, the two proteins assembling into heterodimers. When in that state, the anti-apoptotic member of the Bcl-2 protein family is inactive and it accordingly no longer has its anti-apoptotic activity. In addition, the specific interaction of the BH3 motif with anti-apoptotic members of the Bcl-2 protein family can be modified by modulators so as to bring about programmed cell death in specific manner.

The invention accordingly proposes to screen and identify new peptides which interact with anti-apoptotic members of the Bcl-2 protein family and therefore to use those new peptides to screen and identify compounds that are capable of modifying those interactions in order to obtain real candidate medicaments that are effective in pathologies involving deregulation of apoptosis, especially cancers.

The two-hybrid system consists, to start with, of a test in yeast between two recombined proteins. The first protein, known as the "bait", is a fusion protein containing a DNA binding domain (or BD) bound upstream of a protein A. The second protein is also a fusion protein, commonly known as the "prey", containing an activation domain (or AD) bound to a protein B. The binding and activation domains commonly used are those of Gal4 or *E. Coli* Lex A. Proteins A and B are an anti-apoptotic member of the Bcl-2 protein family and a motif obtained from a cDNA bank, respectively. The association of proteins A and B by protein interaction allows the formation, by complementation, of a functional domain (BD-AD) capable of binding to the binding site (or BS) present upstream of a reporter gene and ensuring the transcription of said reporter gene.

However, this conventional two-hybrid method has its limitations. It is well known, for example, that such screening methods can result in false positives and/or false negatives, and biochemical confirmations of the results obtained are necessary. The false positives obtained by the two-hybrid system are especially frequent and are responsible for demonstrating functional rather than structural interactions.

A more effective technique allowing false positives and/or false negatives to be minimised is described in the International Patent Application WO 99/42612 or the U.S. Pat. No. 6,187,535 and uses recombinant haploid yeasts containing the "bait" and "prey" polypeptides. This system allows detection of a greater number of "preys" using a single "bait" in a more precise, more reproducible and more sensitive manner than the other conventional methods used in the field.

Using the two-hybrid system, the inventors have established the existence of a structural interaction between anti-apoptotic members of the Bcl-2 protein family and the following peptides having amino acid sequences SEQ ID NO.1 to SEQ ID NO.5 according to the invention. This protein interaction between those partners is similar to that which exists in the regulation of the apoptotic phenomenon between anti- and pro-apoptotic partners of the Bcl-2 protein family.

Original peptides having peptide sequences SEQ ID NO.1, SEQ ID NO.2, SEQ ID NO.3, SEQ ID NO.4 and SEQ ID NO.5 have been identified within the context of the invention by the two-hybrid system. Each of those peptides is capable of interacting in highly specific manner with anti-apoptotic members of the Bcl-2 protein family. This specificity of interaction is in fact related to the sequence, the three-dimensional structure and/or the helicity of the original motif of said selected peptide.

Furthermore, these peptides correspond to the precise domain of interaction with Bcl-2, Bcl-$X_L$ and/or Bcl-W and have the typical structural criteria allowing the formation of homo- or hetero-dimers.

The following peptide motif $NH_2$—XXXXXXXX-LXXXXDXXXXXXXXXX—COOH (SEQ ID NO.6), wherein X represents any amino acid, represents a consensus sequence of the peptide sequences SEQ ID NO.1 to SEQ ID NO.5 according to the invention. This consensus sequence is similar to that of the BH3 motifs present in pro-apoptotic members of the Bcl-2 protein family.

Indeed, the size of the peptides according to the invention make them ideal candidates for developing tests allowing highly efficient screening of compounds that are capable of modulating interactions between those peptides and an anti-apoptotic member of the Bcl-2 protein family. Numerous tests are found in the literature for screening modulators of protein-protein interactions but they often have limitations with regard to their sensitivity and their high-throughput feasibility. The methods customarily employed necessitate the use of complex tools (fusion proteins, recombinant proteins etc.) which are not very compatible with high-throughput screening. Very frequently they generate a high level of background noise and are of low reliability from a quantitative point of view: they provide a reduced reading window that does not allow optimum screening of the compounds tested.

As an alternative to the methods already available, a highly efficient screening test based on fluorescence polarisation has been employed in the present invention (Owicki et al., Journal of Biomolecular Screening, 5, 2000, 297-306). This technique allows, for example, measurement of the interaction between a fluorophore-labelled ligand and a receptor. The principle consists of measuring an increase in the polarisation of fluorescence emitted by the ligand when bound to its receptor compared to that emitted by the free ligand. The fluorescence polarisation of the free ligand is dependent on its molecular weight and will be greater the higher the molecular weight. Accordingly, when this test is carried out using a ligand of high molecular weight, having a high level of intrinsic fluorescence polarisation, it will be difficult to reliably evaluate the difference in fluorescence polarisation between the free ligand and the bound ligand. Using a ligand of minimal molecular weight, on the other hand, will allow that difference to be accentuated and consequently allow the precision of the method to be increased. It will accordingly be possible to better evaluate the real activity of a compound and to carry out high-throughput screenings.

The present invention relates to a peptide which interacts with anti-apoptotic members of the Bcl-2 protein family. This peptide contains the following amino acid sequences:

| a) | MATVIHNPLKALGDQFYKEAIEHC; | (SEQ ID NO. 1) |
| b) | VMTQEVGQLLQDMGDDVYQQYRSL; | (SEQ ID NO. 2) |
| c) | RLKHSCLLALKRAADLLGQRSSST; | (SEQ ID NO. 3) |
| d) | DMWDTRIAKLRVSADSFVRQQEA; | (SEQ ID NO. 4) |
| e) | VATRRLSGFLRTLADRLEGTKELL; | (SEQ ID NO. 5) |
| f) | XXXXXXXXLXXXXDXXXXXXXXXX; | (SEQ ID NO. 6) | and functional variants of those amino acid sequences.

An "amino acid sequence" is to be understood as being a peptide sequence isolated from the natural context, especially sequences that have been isolated, chemically synthesised and/or purified and, possibly, modified by genetic engineering.

"Functional variants" are understood as being amino acid sequences of the above-described peptides which comprise conservative substitutions or conservative point mutations and which have substantially the same properties as the peptides respectively encoded by the sequences SEQ ID NO.1 to SEQ ID NO.5 or, that is to say, the ability to interact with an anti-apoptotic member of the Bcl-2 protein family. Conservative substitutions or mutations of the amino acid sequences SEQ ID NO.1 to SEQ ID NO. 5 are, for example, the following: glycine by alanine (G-A), valine by leucine (V-L), aspartic acid by glutamic acid (D-E), asparagine by glutamine (N-Q), arginine by lysine (R-K), tyrosine by leucine (Y-L), leucine by methionine (L-M), valine by isoleucine (V-I) and glutamine by histidine (Q-H).

The invention relates also to the nucleic acid sequences coding for peptides of sequences SEQ ID NO.1 to SEQ ID NO.5. These nucleotide sequences corresponding to the peptide sequences SEQ ID NO.1, SEQ ID NO.2, SEQ ID NO.3, SEQ ID NO.4 and SEQ ID NO.5, respectively, are as follows:

a)
(SEQ ID NO. 7)
atggcgactgtcattcacaacccctgaaagcgctcggggaccagttcta caaggaagccattgagcactgc;

b)
(SEQ ID NO. 8)
gttatgacccaagaggttggccagctcctgcaagacatgggtgatgatgt ataccagcagtaccggtcactt;

c)
(SEQ ID NO. 9)
agacttaaacattcctgcctgctggctctgaagagagcagcggatctcct aggacagcgctcaagctctact;

d)
(SEQ ID NO. 10)
gatatgtgggacactcgtatagccaaactccgagtgtctgctgacagctt tgtgagacagcaggaggca;

g)
(SEQ ID NO. 11)
gttgctacaagacgattaagtggcttcctgaggacacttgcagaccggct ggagggcaccaaagaactgctt.

These nucleic acid sequences according to the invention can be obtained by means of the genetic code starting from the corresponding amino acid sequences and their variants.

The "variants" of those nucleic acid sequences are especially:
sequences that are capable of hybridising under stringent conditions with the nucleic acid sequences SEQ ID NO.7 to SEQ ID NO.11 or sequences complementary thereto and that encode polypeptides having substantially the same properties as the peptides having sequences SEQ ID NO.1 to SEQ ID NO.5, respectively, or
sequences of a mammal species that are homologous to the sequence SEQ ID NO.7 to SEQ ID NO.11 isolated from humans.

"Stringent conditions" are understood to be conditions which allow specific hybridisation of two sequences of single-stranded DNA at about 65° C., for example in a solution of 6×SSC, 0.5% SDS, 5×Denhardt's solution and 100 μg of non-specific carrier DNA or any other solution of equivalent ionic strength, and after washing at 65° C., for example in a solution of at most 0.2×SSC and 0.1% SDS or any other solution of equivalent ionic strength.

The parameters defining the stringency conditions depend on the temperature at which 50% of the paired strands separate (Tm). For sequences comprising more than 30 bases, Tm is defined by the relationship: Tm=81.5+0.41 (% G+C)+16.6 Log (concentration of cations)−0.63 (% formamide)−(600/number of bases). For sequences of less than 30 bases in length, Tm is defined by the relationship: Tm=4 (G+C)+2(A+T). The stringency conditions can accordingly be adapted by the person skilled in the art in dependence on the size of the sequence, the content of GC and any other parameter, especially in accordance with the protocols described in Sambrook et al., 2001 (Molecular Cloning: A laboratory Manual, 3rd Ed., Cold Spring Harbor, laboratory press, Cold Spring Harbor, N.Y.).

"Sequences of a mammal species that are homologous to the sequences SEQ ID NO.7 to SEQ ID NO.11" are understood to be sequences of similar structure to said nucleotide sequences and coding for respective polypeptides having substantially the same properties in non-human species of mammals, especially primates, the rat or the mouse. The percentage identity between two homologous sequences in the functional regions is generally greater than 80%, preferably greater than 90%.

The invention relates also to a recombinant vector containing a nucleic acid sequence, SEQ ID NO.7 to SEQ ID NO.11, as claimed according to the invention. A vector is to be understood as any type of vector allowing introduction of the nucleic acid sequence into the host cell and, optionally, expression—in the host cell—of the polypeptide encoded by the nucleic acid sequence.

Such a vector is, for example, a plasmid, a cosmid, a bacterial artificial chromosome or a bacteriophage, containing the sequences necessary for expression of the peptides having amino acid sequences SEQ ID NO.1 to SEQ ID NO.5.

Preferably, the recombinant vector according to the invention contains the sequences necessary for expression—in the host cell—of the peptides having sequences SEQ ID NO.1 to SEQ ID NO.5. These sequences are especially promoter sequences of transcription and translation in the host cell and also terminator sequences. The recombinant vector can also contain sequences coding for secretion signals allowing release of the translated proteins into the extracellular environment.

The invention relates also to host cells transformed by a recombinant vector according to the invention. In a particular embodiment, those host cells are bacterial cells such as, for example, *Escherichia coli* and streptococci or eukaryotic cells such as yeast cells, filamentous fungi cells, insect cells and, preferably, mammalian cells.

Transformation of appropriate host cells by a recombinant vector containing the nucleic acid sequences according to the invention allows the respective claimed peptides SEQ ID NO.1 to SEQ ID NO.5 to be expressed. Afterwards, it is possible to purify the proteins expressed in those host cells, using various methods known to the person skilled in the art and abundantly described in the prior art. There may be mentioned, for example, purification by precipitation with ammonium sulfate, by size-exclusion chromatography and, preferably, by affinity chromatography.

The peptides having the amino acid sequences SEQ ID NO.1, SEQ ID NO.2, SEQ ID NO.3, SEQ ID NO.4 and SEQ ID NO.5 can also be custom-synthesised chemically by Néosystem. Chemical synthesis of the peptide sequences SEQ ID NO.1 to SEQ ID NO.5 and their functional variants is carried out by synthesis on a solid support using the Boc/benzyl strategy with the aid of an "Applied Biosystems 430A" peptide synthesizer. The synthesis is based on the assembly on resin of the desired sequence and then deprotection of the N-terminal and C-terminal amino functions. In the case of the Boc/benzyl strategy it is necessary to introduce the amino acid Boc-L-Lys(Fmoc)-OH during synthesis of the peptide. After the full sequence has been assembled, the amino function is deprotected and the peptide is cleaved from the resin in the presence of a strong acid.

The invention relates also to a pharmaceutical composition comprising, as active ingredient, a peptide having amino acid sequence SEQ ID NO.1, SEQ ID NO.2, SEQ ID NO.3, SEQ ID NO.4 or SEQ ID NO.5 in combination with one more pharmaceutically acceptable excipients.

In the context of the invention, "excipients" of a pharmaceutical composition are understood to be any agent which ensures that the active ingredient is transported into the internal tracts of the patient being treated. An "active ingredient" is understood to be any substance which is responsible for the pharmacodynamic or therapeutic properties of the pharmaceutical composition.

Among non-toxic, pharmaceutically acceptable excipients there may be mentioned, by way of example and without implying any limitation, diluents, solvents, preservatives, wetting agents, emulsifiers, dispersants, binders, swelling agents, disintegrants, retardants, lubricants, absorbency agents, suspension agents, colourants or flavourings.

The present invention relates not only to the pharmaceutical composition considered as such and defined above but also to the use of that composition in a method of bringing about programmed cell death, said method comprising the administration to a patient, especially a patient with cancer, of an effective amount of pharmaceutical composition comprising one of the peptides according to the invention.

The invention relates also to a method of identifying modulators of interaction between a peptide according to the invention and an anti-apoptotic member of the Bcl-2 protein family, comprising the following steps:
  a) bringing said peptide and said anti-apoptotic member of the Bcl-2 protein family into contact;
  b) addition of the compound under test; and
  c) measurement of the activity of the compound under test as a modulator of the protein interaction between the peptide and the anti-apoptotic member of the Bcl-2 protein family and then comparison of said measurement in the absence of the compound under test.

Advantageously, the method of identifying modulators of the interaction comprises the following steps:
  a) fluorescence labelling of a peptide according to claim 1;
  b) incubation of said peptide in the presence of the compound under test;
  c) addition of an anti-apoptotic member of the Bcl-2 protein family;
  d) measurement of the fluorescence polarisation;
  e) comparison of the measurement with or without the compound under test.

A "modulator" is understood to be any compound capable of increasing, preventing or at least limiting a specific activity such as a protein-protein interaction, enzymatic activity or binding to cellular receptors. In accordance with the present invention, modulators are inhibitors or indeed activators of protein interaction between the partners which are peptides having amino acid sequences SEQ ID NO.1 to SEQ ID NO.5 and anti-apoptotic members of the Bcl-2 protein family.

The invention relates also to a method of identifying an inhibitor of the interaction between one of the peptides according to the invention and an anti-apoptotic member of the Bcl-2 protein family, which is capable of decreasing the fluorescence polarisation compared to a control consisting of this interaction in the absence of modulator.

The invention relates also to a method of identifying an activator of the interaction between one of the peptides according to the invention and an anti-apoptotic member of the Bcl-2 protein family, which is capable of increasing the fluorescence polarisation compared to a control consisting of this interaction in the absence of modulator.

The fluorescent ligand, i.e. a fluorescent peptide motif SEQ ID NO.1 to SEQ ID NO.5, has, after binding with the anti-apoptotic partner of the Bcl-2 protein family, a rotational constant which is lower than the corresponding free ligand and, as a result, the fluorescence emitted by the bound ligand becomes polarised. Consequently, an increase in the polarisation of the fluorescence emitted by the bound ligand is observed, compared to the free ligand.

In a preferred embodiment, the fluorescence probe used in the method of screening and identification according to the invention is Bodipy, Oregon Green or, more preferably, fluorescein.

More particularly, the anti-apoptotic member of the Bcl-2 protein family involved as interaction partner in the process of screening and identification according to the invention can be the protein Bcl-2, Bcl-$X_L$ or Bcl-W.

Advantageously, the anti-apoptotic member of the Bcl-2 protein family is a fusion protein. A "fusion protein" is understood to refer to the fusion between a domain of the protein Bcl-2, Bcl-$X_L$ or Bcl-W and a domain of a protein such as GST (glutathione S-transferase).

The invention relates also to a pharmaceutical composition comprising at least one modulator, activator or inhibitor, identified using the method of identifying modulators in accordance with the invention, as active ingredient of said composition, in combination with one or more pharmaceutically acceptable excipients.

The invention relates also to a method of bringing about apoptotic-type (caspase-dependent) programmed cell death and/or autophagic-type (caspase-independent) programmed cell death by means of the administration of an effective amount of the above-defined composition to a patient with cancer.

The pharmaceutical compositions as described above are suitable for use in the treatment of cancers by action on apoptotic-type and/or autophagic-type programmed cell death.

The compositions according to the invention are in a form suitable for oral, parenteral, nasal, per- or trans-cutaneous, rectal, perlingual, ocular or respiratory administration, especially tablets, dragées, sublingual tablets, sachets, paquets, capsules, glossettes, lozenges, suppositories, creams, ointments, dermal gels and drinkable or injectable ampoules.

The present invention is illustrated, without being limited thereby, by the following Figures and Examples:

FIG. 1: amino acid sequence SEQ ID NO.1 of the Cerd4 peptide which interacts with anti-apoptotic members of the Bcl-2 protein family.

FIG. 2: amino acid sequence SEQ ID NO.2 of the Kiaa 1578 peptide which interacts with anti-apoptotic members of the Bcl-2 protein family.

FIG. 3: amino acid sequence SEQ ID NO.3 of the Genematch peptide which interacts with anti-apoptotic members of the Bcl-2 protein family.

FIG. 4: amino acid sequence SEQ ID NO.4 of the Loc 51569 peptide which interacts with anti-apoptotic members of the Bcl-2 protein family.

FIG. 5: amino acid sequence SEQ ID NO.5 of the Mina53 peptide which interacts with anti-apoptotic members of the Bcl-2 protein family.

FIG. 6: consensus motif SEQ ID NO.6 of the peptide sequences SEQ ID NO.1 to SEQ ID NO.5 according to the invention.

FIG. 7: determination of Ki, using fluorescence polarisation, of the competitor peptides having amino acid sequences SEQ ID NO. 1 to SEQ ID NO.5 according to the invention with respect to the interaction between the pro-apoptotic Bak peptide and the anti-apoptotic member Bcl-$X_L$.

FIG. 8: recapitulatory table of the amino acid sequences SEQ ID NO.1 to SEQ ID NO.5 and their respective nucleic acid sequences SEQ ID NO.7 to SEQ ID NO.11.

EXAMPLE 1

Identification, by the Two-Hybrid System, of the Peptides Described in FIGS. 1 to 5

Three banks of human cDNA (placenta, brain, cell line CEMC7) were screened by the two-hybrid technique (Fields et al.) in yeast using the conjugation protocol described by Legrain et al. in Nature Genetics, 1997, vol. 16, 277-282 (U.S. Pat. No. 6,187,535).

1) Preparation of the "Baits" and "Preys"
a) The "baits" used are:
  the C-terminal truncate (1-209) of Bcl-$X_L$ (accession number Z23115) fused to the LexA DNA binding domain;
  the C-terminal truncate (1-211) of Bcl-2 (accession number XM_008738) fused to the LexA DNA binding domain.

These baits are expressed in *Saccharomyces cerevisiae* yeasts, strain L40Δgal4 (MATa ade2, trp1-901, leu2-3, 112, lys2-801, his3Δ200, LYS2 (lexAop)$_4$-HIS3, ura3-52::URA3 (lexAop)$_8$-LacZ, GAL4::Kan$^R$), and precultured at 30° C. in a synthetic medium lacking tryptophan (DO-Trp) until an optical density DO$_{600nm}$ of between 0.1 and 0.5, inclusive, is obtained. Fifty ml of a dilution of that preculture (DO$_{600nm}$=0.006) are incubated at 30° C. overnight.
b) A collection of *Saccharomyces cerevisiae* yeasts, strain YHGX13 (MATα Gal4Δ Gal80Δ ade2-101::Kan$^R$, his3, leu2-3-112, trp1-901, ura3-52 URA3::UASGAL1-LacZ, Met), containing the plasmids expressing the cDNA banks, fused to the Gal4 transcription activation domain, is obtained by transformation following selection on a culture medium lacking leucine (DO-Leu). These yeasts are divided into aliquots and stored at −80° C.

2) Conjugation

Conjugation is carried out using a "bait"/"prey" ratio of 2. An amount of yeast "bait" cells obtained in Step 1)a) corresponding to 50 units of DO$_{600nm}$ is mixed with the yeast "preys" obtained in Step 1)b). After centrifugation, the sediment is resuspended in a YPGlu medium, spread onto YPGlu culture plates and incubated for 4 hours 30 minutes at 30° C. Selection of the conjugated yeasts containing a "bait" and a "prey" capable of interacting with one another is carried out in a DO-Leu-Trp-His medium: the absence of leucine and tryptophan makes it possible to maintain a selection pressure allowing only those yeasts that contain the two types of plasmid ("baits"/"preys") to grow; the absence of histidine from the medium makes it possible to select the conjugated yeasts containing a "bait" plasmid and a "prey" plasmid capable of interacting with one another: the complementation as described makes it possible to activate the HIS3 gene as a reporter gene coding for an enzyme involved in the biosynthesis of histidine.

3) Identification of Positive Clones

The "prey" fragments of a colony of yeasts selected according to the conjugation method described in paragraph 2) are amplified by PCR starting from a crude lysate of that colony using specific primers of the "prey" vector:

ABS1 5'-GCTTTGGAATCACTACAGG-3';     (SEQ ID NO. 12)

ABS2 5'-CACGATGCACGTTGAAGTG-3'.     (SEQ ID NO. 13)

The PCR products are then sequenced and the sequences obtained are identified by comparison with databases.

4) Identification of the Peptides Described in FIGS. 1 to 5

For each "bait" fragment tested, the two-hybrid system allows a plurality of "prey" fragments to be identified. This identification is carried out by comparison of sequences of the selected "preys" using a software program such as Blastwun, which is available on the website of the University of Washington.

EXAMPLE 2

Validation of the Interaction Between the Peptides Obtained in Example 1 and Bcl-2, Bcl-X$_L$ and/or Bcl-W 1) Determination of Ki Using Fluorescence Polarisation The determination of Ki using fluorescence polarisation consists of measuring the effect of the competitor peptides respectively having amino acid sequences SEQ ID NO.1 to SEQ ID NO.5 on the interaction between the pro-apoptotic Bak peptide and anti-apoptotic members of the Bcl-2 protein family such as Bcl-X$_L$.

The following reagents are mixed together in the order stated:
competitor peptide at a final concentration of from 1 nM to 100 μM;
fluorescent peptide ligand (Bak BH3 carboxyfluorescein) at a final concentration of 15 nM;
anti-apoptotic member of the Bcl-2 protein family at a final concentration of 100 nM for Bcl-X$_L$.

These reagents are dissolved in the interaction buffer (Na$_2$HPO$_4$ 20 mM pH 7.4, EDTA 1 mM, NaCl 50 mM and pluronic acid F-68 0.05%).

The mixture is then incubated for 30 minutes at ambient temperature and the fluorescence polarisation is determined on a Fusion apparatus (Packard) (excitation at 485 nm and reading at 530 nm). The values are given in mP (unit of fluorescence polarisation).

These fluorescence polarisation analyses demonstrated that the peptides having amino acid sequences SEQ ID NO.1 to SEQ ID NO.5 are competitor peptides of the peptide interaction between Bak and Bcl-X$_L$. The Ki values obtained in the course of these fluorescence polarisation tests are as follows:

| | |
|---|---|
| Bcl-X$_L$/Bak/SEQ ID NO. 1 | Ki = 9 μM |
| Bcl-X$_L$/Bak/SEQ ID NO. 2 | Ki = 32 μM |
| Bcl-X$_L$/Bak/SEQ ID NO. 3 | Ki = 1 μM |
| Bcl-X$_L$/Bak/SEQ ID NO. 4 | Ki = 8 μM |
| BCl-X$_L$/Bak/SEQ ID NO. 5 | Ki = 20 μM |

2) Determination of Ki, Using Fluorescence Polarisation, with the Respective Mutant Peptide Motifs (L-A)

The determination of Ki using fluorescence polarisation consists of measuring the competitive effect of the peptides SEQ ID NO.1 to SEQ ID NO.5 that have been mutated from leucine to alanine (L-A) on the interaction between the pro-apoptotic BAK peptide and anti-apoptotic members of the Bcl-2 protein family such as Bcl-X$_L$.

The peptide sequences SEQ ID NO.1 to SEQ ID NO.5 in mutated form (L-A) are as follows:

| | |
|---|---|
| MATVIHNPAKALGDQFYKEAIEHC; | (SEQ ID NO. 14) |
| VMTQEVGQLAQDMGDDVYQQYRSL; | (SEQ ID NO. 15) |
| RLKHSCLLAAKRAADLLGQRSSST; | (SEQ ID NO. 16) |
| DMWDTRIAKARVSADSFVRQQEA; | (SEQ ID NO. 17) |
| VATRRLSGFARTLADRLEGTKELL. | (SEQ ID NO. 18) |

The protocol for the determination of Ki using fluorescence polarisation is the same as the protocol described above.

Comparison of the results of the fluorescence polarisation analyses shows a loss of competitive effect with the mutant (L-A) peptides SEQ ID NO.14 to SEQ ID NO.18 relative to the peptides SEQ ID NO.1 to SEQ ID NO.5 according to the invention in the peptide interaction between the pro-apoptotic Bak peptide and anti-apoptotic members of the Bcl-2 protein family such as Bcl-X$_L$.

EXAMPLE 3

Screening Test for Compounds Capable of Inhibiting the Interaction Between Bcl-2 and/or Bcl-X$_L$ and the Peptides Obtained in Example 1

The compounds under test are distributed on 384-well plates (Corning Flat Bottom) at a final concentration of 10 μg/ml. One well is filled with an equivalent amount of buffer/solvent without a test compound, for use as the control. The peptides obtained in Example 1, labelled with fluorescein, are added to the wells so as to obtain a final concentration ranging from 1 to 100 nM. The fusion protein GST-Bcl-X$_L$, or GST-Bcl-2, or also GST-Bcl-W, is then added so as to obtain a final concentration of from 0.1 to 1 μM in a buffer containing Na$_2$HPO$_4$ 20 mM pH 7.4, EDTA 1 mM, NaCl 50 mM and pluronic acid F-68 0.05%. The fluorescence polarisation is then measured by an En Vision apparatus (Packard Perkin-Elmer). A significant reduction in the fluorescence polarisation recorded in the test carried out with the test compound compared to that obtained without the test compound (control well) allows the conclusion that the compound has inhibitory activity. Conversely, a significant increase in the fluorescence polarisation in the test with the test compound compared to the control allows the conclusion that the compound has activator activity.

The invention claimed is:

1. An isolated peptide which interacts with at least one anti-apoptotic member of the Bcl-2 protein family, wherein the peptide contains the amino acid sequence

RLKHSCLLALKRAADLLGQRSSST    (SEQ ID NO. 3).

2. A method of identifying modulators of an interaction between the peptide of claim 1 and an anti-apoptotic member of the Bcl-2 protein family, comprising:
   a) bringing the peptide and the anti-apoptotic member of the Bcl-2 protein family into contact;
   b) adding a compound under test; and
   c) measuring the ability of the compound under test to modulate the interaction between the peptide and the anti-apoptotic member of the Bcl-2 protein family, and then comparing the measurement with a measurement of the interaction in the absence of the compound under test, wherein a difference in the interaction of the peptide and the anti-apoptotic member of the Bcl-2 protein family in the presence compared to in the absence of the compound indicates the compound is a modulator of said interaction.

3. A method of identifying modulators of an interaction between the peptide of claim 1 and an anti-apoptotic member of the Bcl-2 protein family, comprising the following steps:
   a) labelling the peptide of claim 1 with a fluorescence probe;
   b) incubating the peptide in the presence of the compound under test;
   c) adding an anti-apoptotic member of the Bcl-2 protein family;
   d) measuring the fluorescence polarisation; and
   e) comparing the measurement with or without the compound under test, wherein an increase in the fluorescence polarisation in the presence compared to in the absence of said compound indicates said compound is an activator of an interaction between the peptide of claim 1 and an anti-apoptotic member of the Bcl-2 protein family and wherein a decrease in the fluorescence polarization indicates said compound is an inhibitor.

4. The method of claim 3, wherein the fluorescence probe is fluorescein.

5. The method of claim 3, wherein the anti-apoptotic member of the Bcl-2 protein family is the protein Bcl-2, Bcl-$X_L$ or Bcl-W.

* * * * *

SEQUENCE LISTING

```
<160> NUMBER OF SEQ ID NOS: 18

<210> SEQ ID NO 1
<211> LENGTH: 24
<212> TYPE: PRT
<213> ORGANISM: Homo sapiens

<400> SEQUENCE: 1

Met Ala Thr Val Ile His Asn Pro Leu Lys Ala Leu Gly Asp Gln Phe
1               5                   10                  15
```

Tyr Lys Glu Ala Ile Glu His Cys
            20

<210> SEQ ID NO 2
<211> LENGTH: 24
<212> TYPE: PRT
<213> ORGANISM: Homo sapiens

<400> SEQUENCE: 2

Val Met Thr Gln Glu Val Gly Gln Leu Leu Gln Asp Met Gly Asp Asp
1               5                   10                  15

Val Tyr Gln Gln Tyr Arg Ser Leu
            20

<210> SEQ ID NO 3
<211> LENGTH: 24
<212> TYPE: PRT
<213> ORGANISM: Homo sapiens

<400> SEQUENCE: 3

Arg Leu Lys His Ser Cys Leu Leu Ala Leu Lys Arg Ala Ala Asp Leu
1               5                   10                  15

Leu Gly Gln Arg Ser Ser Ser Thr
            20

<210> SEQ ID NO 4
<211> LENGTH: 23
<212> TYPE: PRT
<213> ORGANISM: Homo sapiens

<400> SEQUENCE: 4

Asp Met Trp Asp Thr Arg Ile Ala Lys Leu Arg Val Ser Ala Asp Ser
1               5                   10                  15

Phe Val Arg Gln Gln Glu Ala
            20

<210> SEQ ID NO 5
<211> LENGTH: 24
<212> TYPE: PRT
<213> ORGANISM: Homo sapiens

<400> SEQUENCE: 5

Val Ala Thr Arg Arg Leu Ser Gly Phe Leu Arg Thr Leu Ala Asp Arg
1               5                   10                  15

Leu Glu Gly Thr Lys Glu Leu Leu
            20

<210> SEQ ID NO 6
<211> LENGTH: 24
<212> TYPE: PRT
<213> ORGANISM: Artificial Sequence
<220> FEATURE:
<223> OTHER INFORMATION: Homo sapiens binding domain
<220> FEATURE:
<221> NAME/KEY: MISC_FEATURE
<222> LOCATION: (1)..(8)
<223> OTHER INFORMATION: Xaa may be any amino acid
<220> FEATURE:
<221> NAME/KEY: MISC_FEATURE
<222> LOCATION: (10)..(13)
<223> OTHER INFORMATION: Xaa may be any amino acid
<220> FEATURE:
<221> NAME/KEY: MISC_FEATURE
<222> LOCATION: (15)..(24)
<223> OTHER INFORMATION: Xaa may be any amino acid

```
<400> SEQUENCE: 6

Xaa Xaa Xaa Xaa Xaa Xaa Xaa Xaa Leu Xaa Xaa Xaa Xaa Asp Xaa Xaa
1               5                   10                  15

Xaa Xaa Xaa Xaa Xaa Xaa Xaa Xaa
            20

<210> SEQ ID NO 7
<211> LENGTH: 72
<212> TYPE: DNA
<213> ORGANISM: Homo sapiens

<400> SEQUENCE: 7
atggcgactg tcattcacaa cccccctgaaa gcgctcgggg accagttcta caaggaagcc      60
attgagcact gc                                                          72

<210> SEQ ID NO 8
<211> LENGTH: 72
<212> TYPE: DNA
<213> ORGANISM: Homo sapiens

<400> SEQUENCE: 8
gttatgaccc aagaggttgg ccagctcctg caagacatgg gtgatgatgt ataccagcag      60
taccggtcac tt                                                          72

<210> SEQ ID NO 9
<211> LENGTH: 72
<212> TYPE: DNA
<213> ORGANISM: Homo sapiens

<400> SEQUENCE: 9
agacttaaac attcctgcct gctggctctg aagagagcag cggatctcct aggacagcgc      60
tcaagctcta ct                                                          72

<210> SEQ ID NO 10
<211> LENGTH: 69
<212> TYPE: DNA
<213> ORGANISM: Homo sapiens

<400> SEQUENCE: 10
gatatgtggg acactcgtat agccaaactc cgagtgtctg ctgacagctt tgtgagacag      60
caggaggca                                                              69

<210> SEQ ID NO 11
<211> LENGTH: 72
<212> TYPE: DNA
<213> ORGANISM: Homo sapiens

<400> SEQUENCE: 11
gttgctacaa gacgattaag tggcttcctg aggacacttg cagaccggct ggagggcacc      60
aaagaactgc tt                                                          72

<210> SEQ ID NO 12
<211> LENGTH: 19
<212> TYPE: DNA
<213> ORGANISM: Artificial Sequence
<220> FEATURE:
<223> OTHER INFORMATION: Primer

<400> SEQUENCE: 12
gctttggaat cactacagg                                                   19
```

<210> SEQ ID NO 13
<211> LENGTH: 19
<212> TYPE: DNA
<213> ORGANISM: Artificial Sequence
<220> FEATURE:
<223> OTHER INFORMATION: Primer

<400> SEQUENCE: 13
cacgatgcac gttgaagtg                                              19

<210> SEQ ID NO 14
<211> LENGTH: 24
<212> TYPE: PRT
<213> ORGANISM: Artificial Sequence
<220> FEATURE:
<223> OTHER INFORMATION: Mutated Peptide

<400> SEQUENCE: 14

Met Ala Thr Val Ile His Asn Pro Ala Lys Ala Leu Gly Asp Gln Phe
1               5                   10                  15

Tyr Lys Glu Ala Ile Glu His Cys
            20

<210> SEQ ID NO 15
<211> LENGTH: 24
<212> TYPE: PRT
<213> ORGANISM: Artificial Sequence
<220> FEATURE:
<223> OTHER INFORMATION: Mutated Peptide

<400> SEQUENCE: 15

Val Met Thr Gln Glu Val Gly Gln Leu Ala Gln Asp Met Gly Asp Asp
1               5                   10                  15

Val Tyr Gln Gln Tyr Arg Ser Leu
            20

<210> SEQ ID NO 16
<211> LENGTH: 24
<212> TYPE: PRT
<213> ORGANISM: Artificial Sequence
<220> FEATURE:
<223> OTHER INFORMATION: Mutated Peptide

<400> SEQUENCE: 16

Arg Leu Lys His Ser Cys Leu Leu Ala Ala Lys Arg Ala Ala Asp Leu
1               5                   10                  15

Leu Gly Gln Arg Ser Ser Ser Thr
            20

<210> SEQ ID NO 17
<211> LENGTH: 23
<212> TYPE: PRT
<213> ORGANISM: Artificial Sequence
<220> FEATURE:
<223> OTHER INFORMATION: Mutated Peptide

<400> SEQUENCE: 17

Asp Met Trp Asp Thr Arg Ile Ala Lys Ala Arg Val Ser Ala Asp Ser
1               5                   10                  15

Phe Val Arg Gln Gln Glu Ala
            20

<210> SEQ ID NO 18
<211> LENGTH: 24
<212> TYPE: PRT

```
-continued

<213> ORGANISM: Artificial Sequence
<220> FEATURE:
<223> OTHER INFORMATION: Mutated Peptide

<400> SEQUENCE: 18

Val Ala Thr Arg Arg Leu Ser Gly Phe Ala Arg Thr Leu Ala Asp Arg
1               5                   10                  15

Leu Glu Gly Thr Lys Glu Leu Leu
            20
```